(12) United States Patent
Varhol

(10) Patent No.: US 6,276,220 B1
(45) Date of Patent: Aug. 21, 2001

(54) MULTIPURPOSE GROUNDWATER SAMPLER

(76) Inventor: Bradley P Varhol, 4320 Horder Ct., Lithonia, GA (US) 30058

( * ) Notice: Subject to any disclaimer, the term of this patent is extended or adjusted under 35 U.S.C. 154(b) by 0 days.

(21) Appl. No.: 09/349,909

(22) Filed: Jul. 8, 1999

Related U.S. Application Data
(60) Provisional application No. 60/092,296, filed on Jul. 10, 1998.

(51) Int. Cl.[7] .............................. G01N 1/00; G01N 1/20; G01N 1/12; G01N 1/04
(52) U.S. Cl. .................................. 73/863.21; 73/863.23; 73/863.71; 73/863.73; 73/864; 73/864.73; 73/864.51
(58) Field of Search .................... 73/863, 863.21, 73/863.22–863.24, 863.71, 863.73, 864, 864.31, 864.51, 864.55, 864.73

(56) References Cited

U.S. PATENT DOCUMENTS

| | | | | |
|---|---|---|---|---|
| 4,745,801 | * | 5/1988 | Luzier | 73/155 |
| 4,949,582 | * | 8/1990 | Vollweiler | 73/864.63 |
| 4,958,528 | * | 9/1990 | Garrison | 73/864.63 |
| 5,139,654 | * | 8/1992 | Carpenter | 210/136 |
| 5,341,692 | * | 8/1994 | Sher et al. | 73/864.63 |

\* cited by examiner

*Primary Examiner*—Hezron Williams
*Assistant Examiner*—Dennis E. Loo
(74) *Attorney, Agent, or Firm*—Hinkle & Associates, PC

(57) ABSTRACT

Embodiments of a multipurpose groundwater sampler device are shown and described, each having a sample tube part of which forms a sample chamber, a top portion having a handle, a novel inlet portion, a sediment trap, novel valve means and a means to join the assembly together. The novel inlet portion is of a size and shape that facilitates rapid filling of the sample chamber and facilitates the collection of layers of fluid which can be measured in the sample chamber to directly represent the in situ thickness of a stratified layer. The novel valve means also facilitates fast filling and incorporates a sediment trap, which keeps sediments from interfering with the valve workings. The multipurpose groundwater sampler device of the present invention is adapted to be provided with an extension tube of the same inside opening as the sample chamber to extend the wide inlet a greater distance from the valve means for collecting thick layers of stratified liquids at their in situ thickness. A novel valve means is disclosed for adaptation to the top portion to prevent the sample chamber from overfilling. The multipurpose groundwater sampler device, may be provided with discharge means to accommodate emptying the sampler.

25 Claims, 3 Drawing Sheets

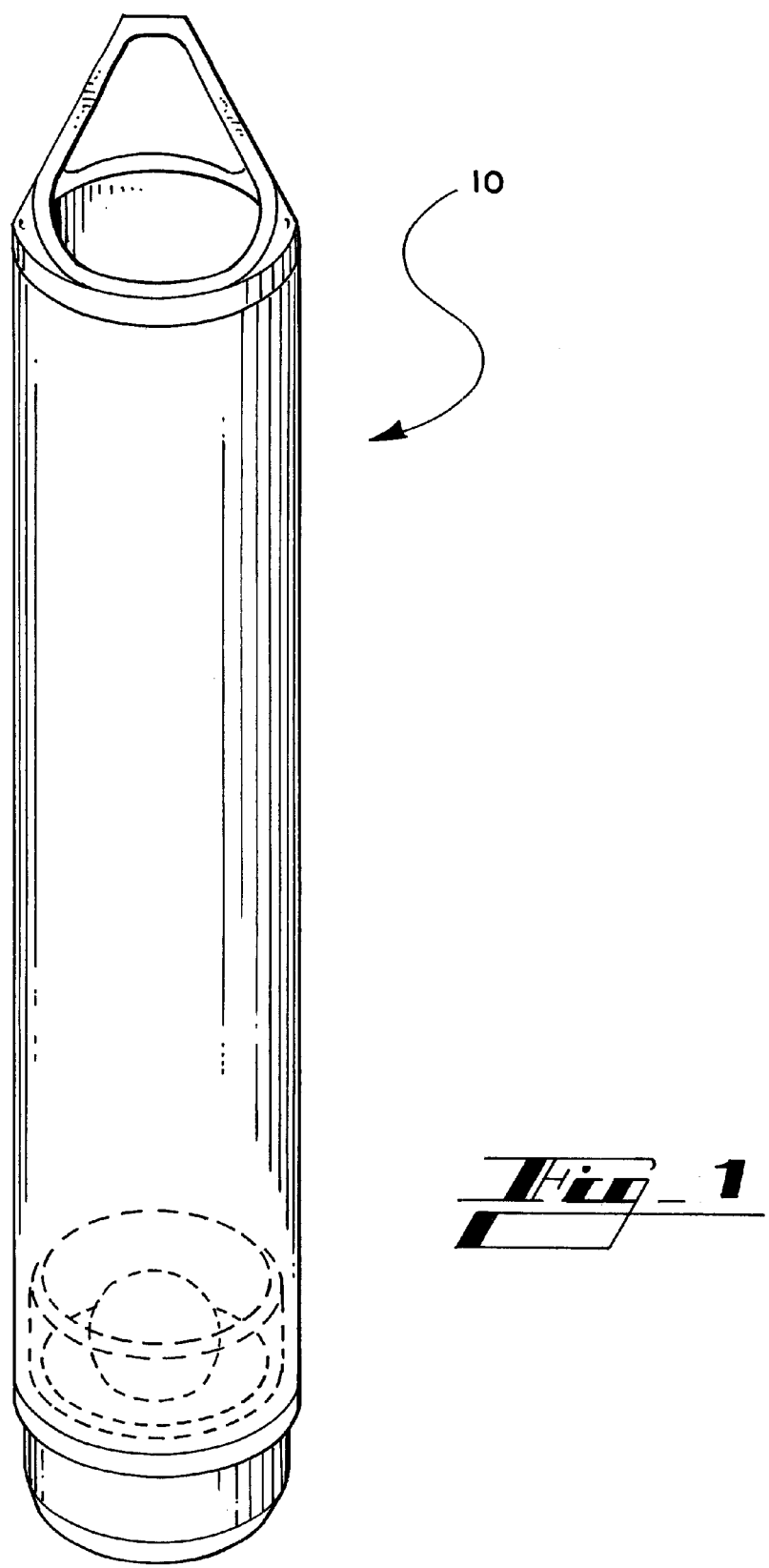
Fig_1

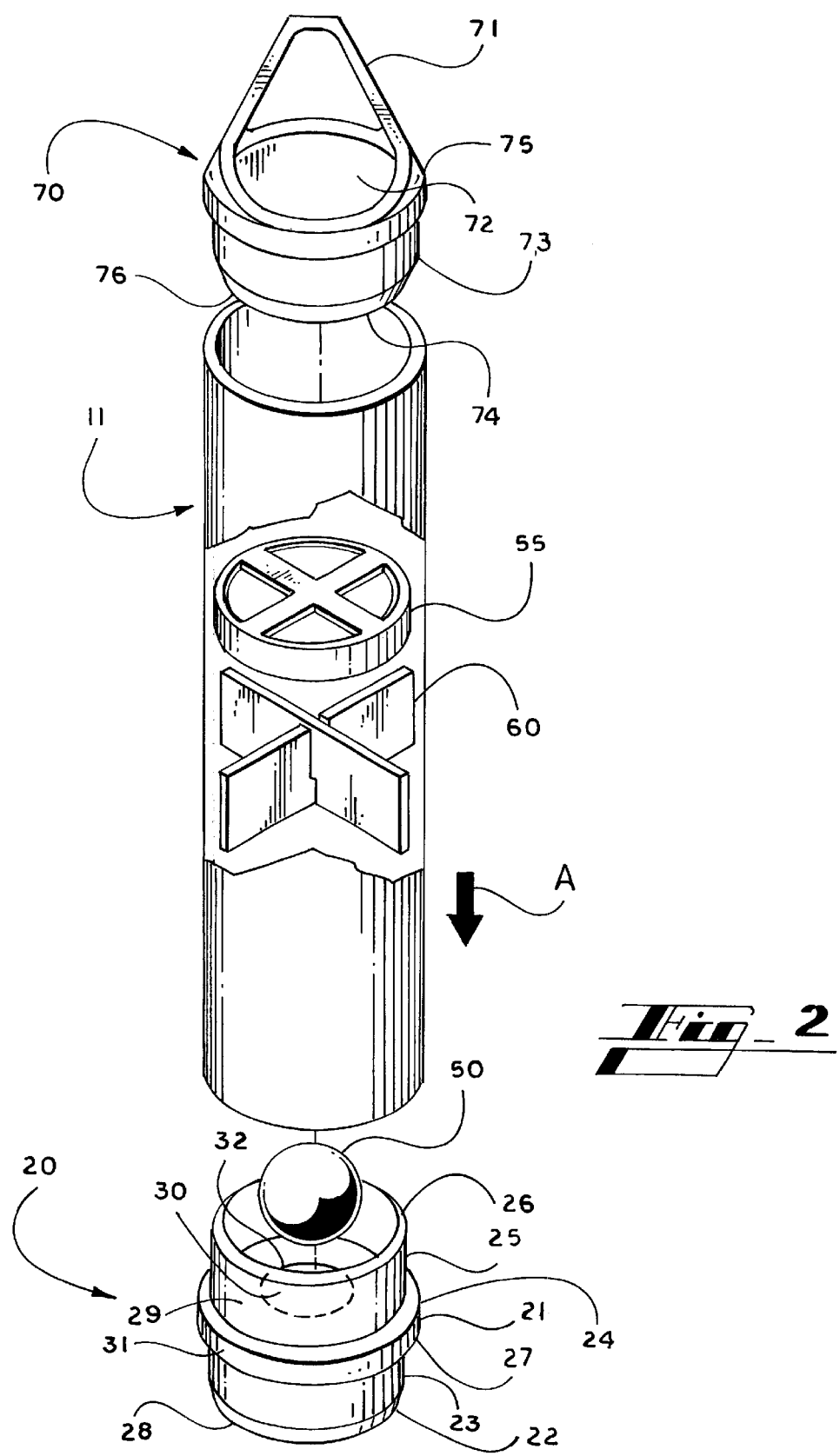
Fig_2

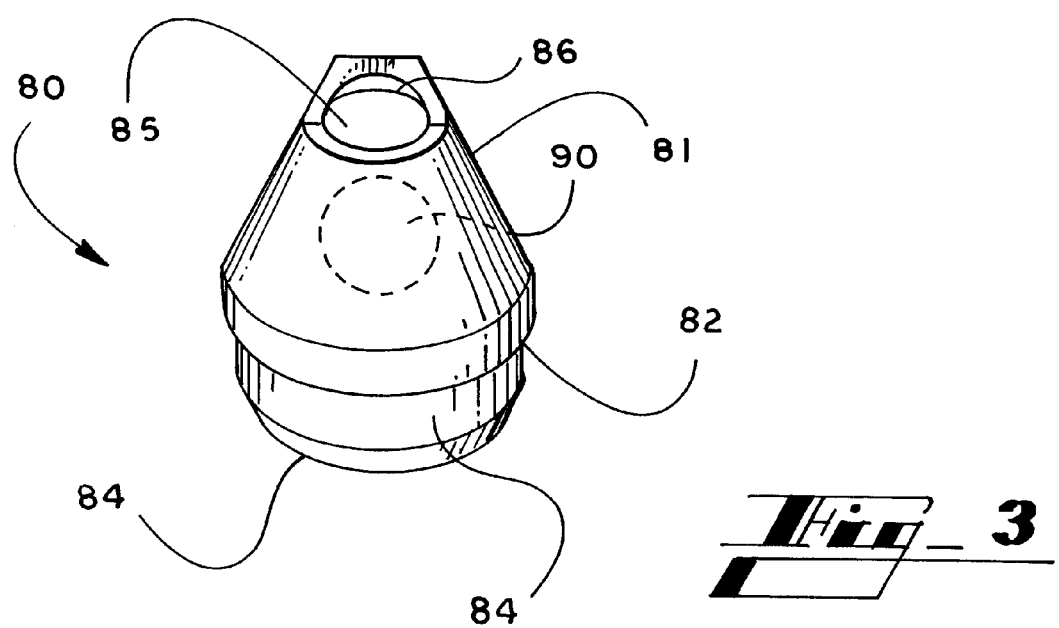
Fig_3
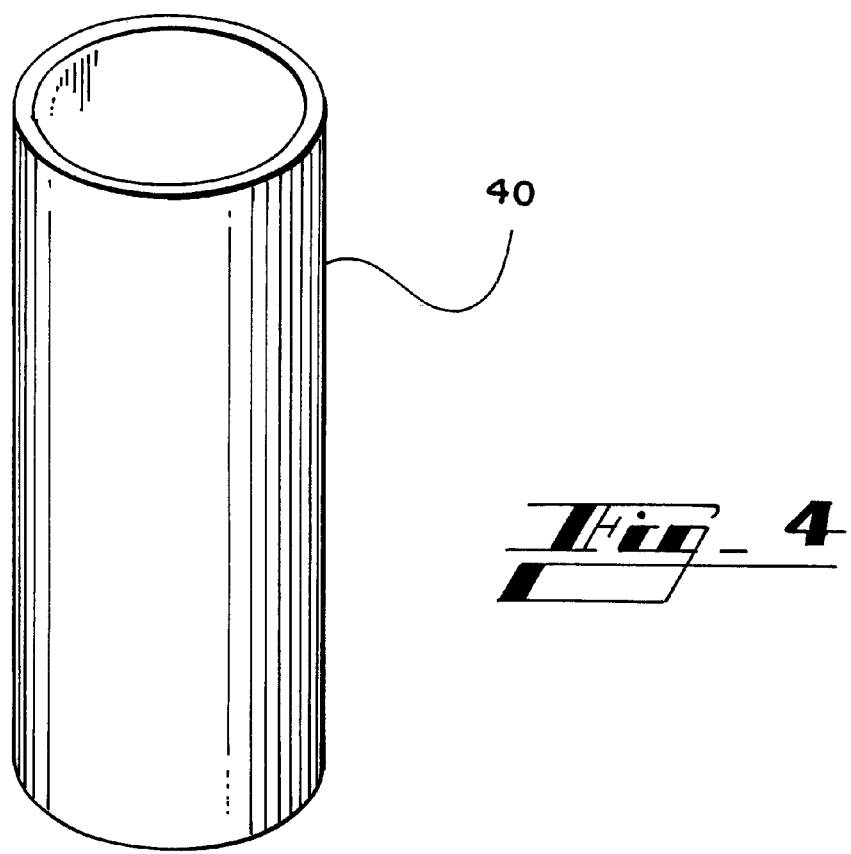
Fig_4

MULTIPURPOSE GROUNDWATER SAMPLER

RELATED APPLICATIONS

The inventor hereof claims priority based upon and pursuant to provisional patent application serial No. 60/092,296 filed on Jul. 10, 1998.

FIELD OF THE INVENTION

This invention relates generally to groundwater contamination sampling systems; and, more particularly, to an apparatus for quickly, accurately, sampling groundwater and accurately and efficiently sampling groundwater where soil sediments or floating contaminants may be present.

BACKGROUND OF THE INVENTION & DESCRIPTION OF THE PRIOR ART

The process of testing groundwater for contamination may be time consuming, expensive, and environmentally unfriendly. Because the results are used to determine future monitoring and/or remediation efforts for which cost can run into millions of dollars, the sampling requires precision. Often it is desirable to retrieve an adequate quantity of chemically and stratigraphically representative samples for analysis. The analysis may include determination of the thickness of a layer of contamination floating on the groundwater surface.

The multipurpose groundwater sampler allows samples to be acquired faster and more efficiently, with less sample loss or interference from sediments and solids and it is quickly field adaptable to retrieve accurate, representative samples of floating contaminant thickness. In accordance with the technique of groundwater sampling, devices of the prior art called bailers are used to retrieve groundwater samples from wells penetrating the water table beneath the ground surface. A bailer consists of a hollow tube with an inlet nozzle and a check valve means at the lower end, and a handle at the top. The bailer is lowered by tether into the well so as to intersect the water table, and fill with water through the bottom nozzle and valve means. The bailer is retrieved to provide a representative water sample for visual and laboratory analysis.

Groundwater sampling bailers of the prior art are commonly produced and sold by a number of manufacturers. These bailers all have certain design features in common which render them inefficient for their intended purpose of sampling groundwater and unreliable for certain other purposes for which there is a concurrent need, such as obtaining a representative thickness of a contaminant, gasoline being an example, floating on the groundwater surfaces. Technicians who use the bailers complain that they fill too slowly and that sediments normally found in the water being sampled cause the devices to leak excessively. Because monitoring sites are remote from a technician's facility, they often complain about the number and amount of equipment they have to carry to complete their sampling.

Voss Technologies produces and sells a makeshift, add-on device for their standard water sampling bailers for those attempting to obtain a sample of floating petroleum contaminants. The device sold by Voss however, has several apparent drawbacks. That device is a separate part which must be purchased, inventoried, brought to the job site, and adapted to a standard bailer. The adapter does not have a means for keeping sediments away from the valve, the adapter has been known to fall off in the well during use, resulting in great expense of time and money attempting retrieval. Further, the device is physically constrained with a fixed distance between the restrictive valve and the fluid inlet with no provision for extending the length in the field to accommodate thicker contaminant layers.

All the groundwater sampling bailers heretofore known suffer from a number of disadvantages and drawbacks:

a) They are made specifically for the one purpose of retrieving a sample of water from below the static water surface. In addition to retrieving a water sample, field technicians often are required to retrieve and measure a representative thickness of floating contaminants such as gasoline. Because it is inconvenient and expensive to carry a multitude of different sampling equipment to each site, technicians attempt to use water-sampling bailers to retrieve a sample of representative thickness of liquids that float on the groundwater surface. Bailers of the prior art are not effective for this purpose because the fluid inlet nozzle is much smaller in diameter than the sample chamber into which the sample is collected. Known bailers of the prior art have nozzle inlet openings of about one half inch in diameter or less to fill a one and one half inch diameter sample chamber. When a bailer with a one half inch diameter nozzle is used to sample a liquid with one inch of stratified contaminant thickness in situ, the bailer will allow less than less than one quarter inch thickness of this layer to accumulate in a one and one half inch diameter sample chamber. The small opening also creates an aerodynamic shape which causes liquids to flow preferentially around the nozzle instead of into the nozzle as the device is lowered into the liquid to be sampled. The thickness of the sample in the sample chamber therefore, is not representative of the fluid thickness in the well.

b) A low cost and reliable device isn't available for retrieving a representative thickness of floating contaminant as well as a representative water sample.

c) Where attempts have been made to provide an adapter to a standard bailer to provide a wider inlet, the attempts have produced devices with inconvenient and expensive add on accessories that can be forgotten or lost and which require the user to know in advance of sampling whether or not the device will be needed., additionally, the add on parts can and do fall off in the well.

d) They fill slower than desired. The small fluid inlet nozzle and its configuration restricts water flow into the sampler such that only a small volume of fluid enters the nozzle relative to the rate of penetration of the sampler through the contaminant and the device fills slower than desired. Frequently, the small diameter, fluid inlet nozzle facilitates the formation of a meniscus across the nozzle that further restricts the flow of water into the sampler.

e) The exteriors are aerodynamically designed having a tapered or dome shaped bottom that is small at the inlet nozzle, becoming larger at the exterior of the sample chamber, as a result, fluids tend to flow preferentially around the outside of the sampler as it is lowered rather than enter the small fluid inlet nozzle. Layers can be missed and sample time is increased.

f) All existing bailers rely on a one way check valve to let fluid in but not back out. Most bailers of the prior art utilize a ball check, valve, others a flapper or pop-it for this valve, which is located at the extreme bottom of the interior of the sampler. All bailers of the prior art have the valves located at the extreme bottom of the sample chamber. Sediments and solids normally present in the water sample settle out of suspension to the lowest point in the sample chamber where they interfere with the workings of the valve. This condition is made worse in bailers where balls serve as valves, by plugging an inlet hole because the ball rests in the small end of a cone shaped holder which funnels and concentrates sediments directly to the area where the ball is expected to produce a seal. The solids and sediments become trapped under and around the ball, propping it away from its mating sealing surface and causing it to leak excessively, resulting in loss of sample and the need for subsequent re-sampling. Further, the excessive leaking causes potentially contaminated fluid to be released into the surrounding environment or splash the user, which may cause harm.

g) Floating contaminants can be lost out the open tops of the bailers if the technician lowers the bailer below the top surface of the water in the well. Bailers of the prior art that utilize a standard check valve at the top of the sample chamber do not address this problem because the valves are in-line and open in the same direction. Fluid flowing in from the bottom can flow right out the top, therefore continued lowering over fills the bailer. Since the device is usually out of sight at some depth, the technician cannot always know when the chamber is full, but not too full.

h) By their nature, valves used to seal the sample chamber of bailers are restrictive to flow. That is, the passageway through which water flows from the well to the sample chamber is smaller than sampler itself, the inlet, and the sample chamber. Those skilled in the art of valves and fluid flow recognize that valves of this type further create physical impediments to water flow. Bailers of the present art are limited in capability because they are constructed with a fixed distance between the fluid inlet and the restrictive valve. The thickness of floating contaminants can vary greatly from well to well. when the contaminant is a thicker layer it will reach the valve restriction before the full thickness is entrapped. The restriction causes the fluid to enter more slowly while the sampler continues descending at the same rate, thereupon pushing aside some of the sample rather than collecting it. Prior art, including add on devices, do not provide a means for the user to make changes in the field to increase the distance between the fluid inlet and the valve restriction to allow a representative thickness of the floating contaminant to enter and be trapped in the sampler prior to its reaching the valve restriction.

It is readily apparent that an improved and multipurpose groundwater sampler is needed to overcome the drawbacks apparent in the prior art and to render more a reliable, convenient, and cost effective method of sampling groundwater and floating liquid thickness. It is, therefore, to the provision of such an improved multipurpose groundwater sampler that the present invention is directed.

OBJECTS AND ADVANTAGES

Accordingly, the several objects of the present invention are:

a )to provide a multipurpose groundwater sampler that causes solids and sediments to be channeled and collected away from the valve means;

b) to provide an improved multipurpose groundwater sampler that provides flexibility of use for the multiple purposes of groundwater sampling and for obtaining representative sample thickness of floating contaminants c) to provide an improved multipurpose groundwater sampler with fewer parts than makeshift attempts at adaptation for multiple purposes;

d) to provide an improved multipurpose groundwater sampler that fills rapidly;

1) to provide an improved multipurpose groundwater sampler that is designed for efficient flow into the sampler instead of around the outside of the sampler.

e) to provide an improved multipurpose groundwater sampler that can be used to accurately recover a representative thickness of floating liquid;

1) to provide an improved multipurpose groundwater sampler with an inlet opening nearly the same diameter as the sample chamber 2) to provide an improved multipurpose groundwater sampler that provides field adaptability for extending the distance from the fluid inlet to the valve means to trap the floating product at its original thickness before the sample reaches the valve means;

3) to provide an improved multipurpose groundwater sampler that readily allows the addition of extension tubes of any length below the valve means 4) to provide an improved multipurpose groundwater sampler for retrieving representative thickness of thin layers of floating contaminants without add on pieces.

f). to provide an improved multipurpose groundwater sampler that can be configured with a floating ball check means at the top to prevent samples from escaping out the top, yet readily fills.

I) to provide an improved multipurpose groundwater sampler that is economical to manufacture;

j) to provide an improved multipurpose groundwater sampler that is reusable for multiple sampling, yet may also be disposable at the end of its service life.

Other objects, features and advantages of the present invention will become apparent to those skilled in the art by reference to the drawings and to the detailed description of the preferred embodiment presented herein.

BRIEF SUMMARY OF THE INVENTION

In accordance with the several objects of the present invention, disclosed is a multipurpose groundwater sampling device having a novel fluid inlet, a novel valve means incorporating an inverted funnel, an elevated valve means on a pedestal structure, a sediment trapping means, an extended wall shank to accommodate an extension inlet tube as an optional feature, a mid portion to contain the sample, a top portion having a handle and a large opening which serves as a pour spout, an optional top portion incorporating a floating valve means, and means to join the assembly together.

The multipurpose groundwater sampler of the present invention is designed to be provided with an optional extension inlet tube of variable length, which can readily be attached to the device in the field, and in which to secure the entire thickness of a floating liquid prior to the liquid reaching the restrictive valve means. The multipurpose groundwater sampler may be provided with weights to overcome any tendency toward buoyancy.

BRIEF DESCRIPTION OF THE DRAWINGS

The invention is better understood by reading the Detailed Description of the Preferred Embodiments with reference to the accompanying drawing figures, in which like reference numerals denote similar structure and refer like elements throughout, and in which:

FIG. 1 is a perspective view of the Multipurpose Groundwater Sampler.

FIG. 2 is an exploded view of the Multipurpose Groundwater Sampler of the present invention with detail.

FIG. 3 is a perspective view of the optional top portion with a floating valve means.

FIG. 4 is a perspective view of the optional extension tube.

It is to be noted that the drawings presented are intended solely for the purpose of illustration and that they are neither desired nor intended to limit the invention to any or all of the exact details of construction shown, except insofar as they may be deemed essential to claim the invention.

REFERENCE NUMERALS IN DRAWINGS

10 Multipurpose Groundwater
11 sample tube
20 valve means structure
21 flange
22 lower tapered edge
23 tower extended wall, shank
24 shoulder
25 upper extended wall, shank
26 upper tapered edge
27 shoulder
28 fluid inlet
29 inverted funnel
30 valve means fluid outlet
31 inverted funnel base
32 valve means seat
40 extension tube
50 ball
55 sample chamber
60 weight means
70 top portion
71 handle
72 pour spout
73 extended wall, shank
74 tapered edge
75 shoulder
76 fluid inlet
80 optional top portion
81 handle
82 extended wall, shank
83 tapered edge
84 pour spout
86 upper ball seat
90 floating ball

DETAILED DESCRIPTION OF THE PREFERRED EMBODIMENT

In describing preferred embodiments of the present invention illustrated in the figures, specific terminology is employed for the sake of clarity. The invention however, is not intended to be limited to the specific terminology so selected, and it is to be understood that each specific element includes all technical equivalents which operate in a similar manner to accomplish a similar purpose.

Shown in FIG. 1 is the preferred embodiment of the multipurpose groundwater sampler 10 of the present invention. In that figure the multipurpose groundwater sampler 10 is shown oriented vertically, that being the principal axis of the sampler while in operation according to its intended use.

In the exploded view of the preferred embodiment shown FIG. 2, the central portion of the multipurpose groundwater sampler 10 is a thin wall, hollow tube or sample chamber 11 of circular cross section. In the preferred embodiment shown in FIG. 2, tube 11 is approximately 1.60 inches in outside diameter and approximately 1.50 inches inside diameter and approximately 36 inches long and is manufactured from extruded High Density Polyethylene (HDPE). At the base of tube 11 as it is shown in FIG. 2, is an appropriately dimensioned novel valve means structure 20. It will be recognized by those skilled in the art of groundwater sampling that the diameter, wall thickness and length are selected with consideration to the structure in which they are placed and the volume of sample required and that the material of manufacture is selected on the basis of chemical compatibility with and nature of the contaminant being sampled, and the structural requirements. Therefore the physical dimensions and the materials of construction may be varied to provide a sampler which fits the intended use.

Valve means structure 20 shown in FIG. 2 is approximately 1.5 inches long, which may vary in proportion to the size of tube 11 with which it is used. Valve means structure 20 shown in the preferred embodiment can be produced as a distinct unit by injection molding, stamping, or machining or as an assembly of separate parts. Alternately, the novel valve means structure 20 may formed into the structure of the main tube body itself by molding or other means.

The exterior of novel valve means structure 20 consists of a generally cylindrical upper extended wall or shank portion 25. The top tapered edge 26 is beveled on the exterior to facilitate insertion of shank 25 into tube 11. The outside diameter of shank 25 is approximately the same dimension as the inside diameter of tube 11 to produce a strong interference fit between tube 11 and shank 25 of the valve means structure 20. A shoulder portion 24 is provided to offset the shank 25 from the flange 21 and against which sample chamber 11 abuts when assembled. The connection between the tube 11 and shank 25 produces a watertight fit. O rings, plumbing tape, or other sealant may be utilized to produce a seal as well. The embodiment of the present invention illustrated in FIG. 2 is assembled by inserting extended wall portion 25 into sample chamber 11 for an interference fit and then heat welding for strength. It will be recognized by those skilled in the art of mechanical connections, however that other mechanical means, such as clamping, screwing, riveting, sonic welding or other means may be utilized in lieu of a friction fit and heat welding.

Shown in FIG. 4 is a generally cylindrical, lower or shank 23 suitable for adaptation to a novel extension tube 40 of the same inside diameter as sample chamber 11 is provided. The bottom leading edge 22 is beveled on the exterior to facilitate insertion of shank 23 into extension tube 40. The outside diameter of lower shank 23 is approximately the same dimension as the inside diameter of extension tube 40 to produce a strong interference fit between extension tube 40 and lower extended wall shank 23 of valve means structure 20. A shoulder portion 24 is provided to offset the lower extended wall shank portion 23 from flange 21 and against which extension tube 40 abuts when assembled. The connection between extension tube 40 and lower shank 23 produces a watertight fit. O rings, plumbing tape, or other sealant may be utilized to produce a seal as well. Extension tube 40 is secured in place by the friction fit or, alternatively, heat welding, clamping, screwing, riveting, sonic welding, or other means of mechanical attachment can be performed at spots along the circumference where tube 11 overlaps shank 25.

Novel valve means 20 contains fluid inlet 28 located at the bottom of valve means assembly 20. Fluid inlet 28 of the preferred embodiment in FIG. 2 is circular in cross section, concentric to tube 11, and has an inside diameter of nearly the same dimension as the inside diameter of tube 11. The diameter of the fluid inlet opening is a minimum of fifty percent the diameter of the inside diameter of the sample chamber Fluid inlet 28 of the preferred embodiment in FIG. 2 has an inside diameter of approximately 1.375 inches. Optional extension tube 40 has an inlet diameter and interior diameter exactly the same as inside diameter of tube 11 sample chamber. The inlet diameter will change according to the diameter of tube 11 used, the material of manufacture, and the structural requirements of the use.

Valve means structure 20 has an internal fluid passageway oriented along the long axis of and concentric to the diameter of valve means structure 20 such that fluid entering at fluid inlet 28 is conducted through the internal passageway to valve means outlet 30. The interior passageway is circular and concentric to tube 11 at all points along its length. The interior diameter remains consistent at approximately 1.375 inches for a distance of approximately 0.625 inches from fluid inlet 28 toward fluid outlet 30. Beginning at a distance of 0.625 inches from fluid inlet 28, the diameter of the passage varies in inverse proportion to the distance from fluid inlet 28 such that the passageway narrows to produce the shape of an inverted funnel 29. Inverted funnel 29 has its largest diameter near fluid inlet 28 and its smaller diameter pointing upward to form valve means outlet 30. The base of inverted funnel 29 is joined to the interior wall of valve means structure 20 circumferentially at approximately the mid point of the long axis of valve means structure 20. The surface of the inverted funnel 29 creates a barrier between the upper interior of valve means structure 29 and the lower interior.

The upper portion of inverted funnel 29 is truncated by a circular opening approximately 0.6875 inches in diameter, concentric with tube 11 and which is valve means outlet 30 from the valve means passageway. Valve means outlet 30 at the top of funnel 29 is located vertically above the base of inverted funnel 29. Inverted funnel 29 thus positioned, functions as a pedestal which serves to elevate check ball 50 or other valve means closure mechanism above the bottom of the interior of tube 11 sample chamber. The top of inverted funnel 29 which forms fluid outlet 30 is beveled inward toward the opening around the entire valve means opening circumference, according to a formulae known in the art of valve seals and seats, to produce a valve means seat 32 against which a spherical ball 50 or other stopper, plug, or other valve means can fit to create a one way seal. Spherical ball 50 shown in the preferred embodiment of FIG. 2 is made of a suitably inert material having a specific gravity greater than the fluid to be sampled, and has a diameter of 0.75 inch, sized in accordance with known principles for utilizing a ball to plug the opening at the top of a circular opening such as in valve means outlet 30. The preferred embodiment shown in FIG. 2 utilizes ball 50 to plug the opening, however it will be readily apparent to those skilled in the art of valves that other manner of sealing devices including flappers and pop-its serve the same purpose.

In the preferred embodiment shown in FIG. 2, the distance from valve means seat 32 to the inside wall of shank 25 of valve means structure 20 is determined by the novel formula to be equal to or is less than the radius of ball 50. If seat 32 is closer to the inside surface of the nearest side wall of tube 11 than it is to the interior surface of shank 25 then this distance is determined by a novel formulae to be equal to, or less than the radius of ball 50 so that the ball will always fall into the seat, by force of gravity, when the sampler is oriented in or near its vertical position as shown in FIG. 1 and the fluid pressure has equilibrated.

$$(d \geq r)$$

Where:
  d is the distance from the outer edge of valve means seat 32 to valve means structure interior wall 27
  r is the radius of ball 50

It will be recognized by those ordinarily skilled in the art that the length and diameter of novel valve means 20 and its functional components typically are selected with consideration to the diameter of the tubing into which they are affixed which is selected with consideration to the size of the well being sampled and the volume of sample specimen required. In that regard, the length and diameter of the novel valve means 20 may be varied in geometric proportion, according to a formula well known in the art, in order to secure the required testing volume and to conform to the physical structure into which it is placed. The various other components of the invention, each of which are to be discussed and described more fully herein below, would then be sized to function effectively with the dimensions of the valve means 20 so selected. Similarly, the composition of the multipurpose groundwater sampler itself and the various components from which it is constructed may be altered to provide or enhance properties suitable and appropriate for use in groundwater sampling.

Top portion 70 is provided consisting of handle 71 and an opening through the center of top portion 70 to tube 11 serving as pour spout 72. Circular opening 76 truncates the bottom of top portion 70. At the bottom of top portion 70 is a generally cylindrical, lower extended wall portion or shank 73 suitable for adaptation to tube 11. Bottom leading edge 74 is tapered on the exterior to facilitate insertion of lower shank 73 into tube 11. The outside diameter of lower extended wall shank 73 is approximately the same dimension as the inside diameter of tube 11 to produce a strong interference fit between tube 11 and lower extended wall shank 73 of top portion 70. A shoulder portion 75 is provided to offset lower shank 73 from the major diameter of top portion 70 and against which tube 11 abuts when assembled. The connection between tube 11 and lower shank 73 produces a watertight fit. O-rings, plumbing tape, or other sealant may be utilized to produce a seal as well. Top portion 70 is secured in place by heat welding at spots along the circumference where tube 11 overlaps shank 73. Alternately clamping, screwing, riveting, sonic welding or other means of mechanical attachment can be performed.

FIG. 3 illustrates optional top portion 80 which can replace top portion 70 for special purposes of preventing fluids in sample chamber 11 from escaping out top portion 80 if the sampler continues to descend in the well after tube 11 is full. Optional top portion 80 consists of a handle 81 and an opening through the center of top portion 80 to tube 11 serving as a pour spout pour spout 85. Opening 85 is circular and concentric to tube 11 and to top portion 80. Opening 85 is approximately 0.625 inches in diameter and is beveled inward on its interior bottom surface according to a formulae known in the art of valve seals and seats, to produce a valve means seat 86 against which a spherical ball 90 or other stopper, plug, or other valve means can fit to create a one way seal which will remain in the open position until fluid rises to the top of inside of tube 11 sample chamber. Spherical ball 90 shown in the preferred embodiment of FIG. 3 is made of a suitably inert material having a specific gravity less than the fluid to be sampled such that it floats, and has a diameter sized in accordance with known principles for utilizing a ball as a valve means to plug the circular opening at top portion 80. In the embodiment, ball 90 is 0.75-inch diameter.

At the bottom of top portion 80 is a generally cylindrical, lower extended wall portion or shank 83 suitable for adaptation to tube 11. Bottom leading edge 84 is tapered on the exterior to facilitate insertion of lower shank 83 into tube 11. The outside diameter of lower shank 83 is approximately the same dimension as the inside diameter of tube 11 to produce a strong interference fit between tube 11 and lower shank 83 of top portion 80. A shoulder 82 offsets lower shank 83 from the major diameter of top portion 80 and against which tube 11 abuts when assembled. The connection between tube 11 and lower shank 83 produces a watertight fit. O-rings, plumbing tape, or other sealant may be utilized to produce a seal as well. Top portion 80 is secured in place by heat welding at spots along the circumference where tube 11 overlaps shank 83. Alternately clamping, screwing, riveting, sonic welding, or other means of mechanical attachment can be performed.

Accordingly, in the embodiment of the of the tube 11 1illustrated in FIG. 2, cross piece 55 is positioned above valve means 20 in tube 11 a sufficient distance so as not to interfere with the operation of valve means 20. Cross piece 55 is generally circular in the shape of a disk with openings through the flat face that allow easy transmittal of water through tube 11 but sized to prevent ball 50 from rolling through the openings along the length of tube 11. Cross piece 55 has a diameter consistent with the inside diameter of tube 11, in this embodiment, 1.50 inches, and is therefore held in place by a tight friction fit between its circumference and the inside circumference of tube 11. An optional weight means 60 may be installed inside sample chamber 11 and held in place by one or more cross pieces 55 or by a friction fit between the outside edges of the weight means 60 and the inside circumference of tube 11.

Having thus described exemplary embodiments of the present invention, it should be noted by those ordinarily skilled in the art that the within disclosures are exemplary only, and that various other alternatives, adaptations, and modifications may be made within the scope of the present invention. Accordingly, the present invention is not limited to the specific embodiments as illustrated herein, but is limited only by the following claims.

I claim:

1. A multipurpose groundwater sampler device for obtaining representative samples of liquids comprising:

a sample tube having an upper end and a lower end, said sample tube having an opening at said upper end of said sample tube and an opening at said lower end of said sample tube and a hollow interior cavity forming a sample chamber, for receiving fluids, and said sample tube optionally employing a weighting means to facilitate submersion of the multipurpose groundwater sampler device; and said upper end carrying a handle for attaching a tether or for grasping said sample tube for the purpose of submersing and withdrawing said sample tube from a liquid; and said upper end carrying a pour spout for discharging sampled liquid, and means carried by said upper end of said sample tube for discharging liquid from said sample tube when optional valve is utilized, said sample tube having an opening at said lower end, said opening serving as an inlet through which liquids to be sampled are conveyed to the interior of the groundwater sampler, driven by the known principle of displacement as said multipurpose groundwater sampler is lowered through said liquid, said lower end of said sample tube carrying means for directionally sealing said sample chamber, thereby maintaining sampled liquid inside said sample chamber, and with means carried by lower end of said sample tube for conducting sample liquid through said sealing means, to said sample chamber, and with discharge means for withdrawing sample from said sample chamber, wherein said multipurpose groundwater sampler device is then removed from the liquid being sampled and a sample of the liquid contained within said sample chamber is observed and measured to determine the presence and the thickness of any stratified layers and then the sample is discharged via said discharge means at said upper end of said sample tube or via said discharge means at said lower end of said sample tube for the analytical measurement of contaminants within the sampled liquid, thus correlating the amount of contaminants within the liquid to those from the in situ source liquid, said multipurpose groundwater sampler device has said inlet means of predetermined geometric proportions which entraps and conducts the liquid through said sealing means into said sample chamber as said sampler is lowered through the liquid such that the thickness of a layer of a stratified liquid in the sample chamber is measurably the same as the thickness of the same stratified layer in-situ, said multipurpose groundwater sampler device carrying sediment trapping means whereby sediments which fall from suspension inside said sample chamber are diverted from said valve means and are separated from liquid discharged for analysis said multipurpose groundwater sampler device carrying means at said lower end of said sample tube for optionally attaching an extension tube, said extension tube having an open upper end and an open lower end and hollow interior cavity, forming a conduit through which liquids may flow, said extension tube functionally extending the inlet opening distance from said valve means whereby said opening at lower end of said extension tube functions as the extended inlet opening of said multipurpose groundwater sampler device, said upper end of sample tube optionally carrying means to directionally seal said sample tube whereby said sealing means prevents liquid from escaping from said sample chamber when said sample chamber is full of liquid, wherein said valve means is elevated above the lowest point on the inside of said sample chamber, and wherein said valve seat and said inside wall of said sample chamber are concentric circles such that the distance from the outer edge of said valve seat to the inside wall of said sample chamber is less than or equal to the radius of said ball, said valve seat structure not to exceed the diameter of said ball, said annulus formed wherein sediments and solids settle out of suspension and accumulate, said annulus located vertically below and away from said valve seat and from said discharge means at lower end of said sample tube, between said valve seat support structure and said inside wall of said sample chamber, thereby preventing interference by sediments with said valve sealing means and reducing unwanted sediments in the liquid sample.

2. The multipurpose groundwater sampler device of claim 1, wherein said material of manufacture is selected on the basis of chemical compatibility with, and the nature of the contaminant being sampled, in conjunction with the structural requirements.

3. The multipurpose groundwater sampler device of claim 2, wherein said material of construction is selected from the group consisting of plastics, metal, fluorocarbon-based polymers, and glass.

4. The multipurpose groundwater sampler device of claim 1, wherein said sealing means at lower end of said sample tube is a check valve selected from the group consisting of ball check valves and flapper check valves and needle check valves.

5. The multipurpose groundwater sampler device of claim 1, wherein the inlet means has an opening of a predetermined size such that when intersecting a cross sectional area of liquid of about the same diameter as the inside diameter of said sample chamber, the inlet opening causing the circumscribed portion of liquid to flow preferentially into said inlet as the multipurpose groundwater sampler device is lowered through the body of liquid.

6. The multipurpose groundwater sampler device of claim 5, wherein said inlet means forms an opening of about the same diameter as the inside diameter of said sample chamber, said opening forming the large end of a funnel shaped conduit, said conduit connecting said inlet opening to said valve means, the smaller end of said funnel shaped conduit oriented upward with respect to the sampler alignment and forming the outlet port of said valve means, said outlet port located inside said sample chamber such that liquid enters said inlet means opening and is conducted through said funnel shaped conduit whereupon the liquid is discharged into said sample chamber.

7. The multipurpose groundwater sampler device according to claim 6, wherein the calculated cross sectional area of said inlet opening is a minimum of twenty percent of the cross sectional area of the inside diameter of said sample tube.

8. The multipurpose groundwater sampler device according to claim 1, wherein said extension tube is of the same inside diameter as said sample tube.

9. The multipurpose groundwater sampler device according to claim 1, wherein said attaching means is selected from the group consisting of interference compression fit, screw threads, snaps or rivets, welding, and clamping.

10. The multipurpose groundwater sampler device of claim 1, wherein said optional valve means at upper end of sample tube is a ball check valve utilizing a ball having a specific gravity less than the sampled liquid said ball floating on said sampled liquid, said ball seat located vertically above said ball at upper end of said sample chamber.

11. A fluid sampling apparatus, comprising:
an elongated tube having and upper end and a lower end;
a valve mechanism having an upper wall, a lower wall and a flange located between the upper and lower walls, wherein the upper and lower walls and the flange surround an inverted funnel having a sealing device, and wherein the upper wall is connected to the lower end of the tube, whereby the valve mechanism is elevated above the lowest point on the inside of the tube; and
a top portion connected to the upper end, the top portion having an upper closed end and an open lower end, and a surrounding wall including a spout exposing the interior of the top portion.

12. The apparatus of claim 11 wherein the lower wall of the valve mechanism forms a fluid inlet having a diameter proportioned to the inside diameter of the tube.

13. The apparatus of claim 11 wherein the lower wall of the valve mechanism forms a fluid inlet having a diameter greater in diameter than approximately one half of the inside diameter of the tube.

14. The apparatus of claim 11 wherein the lower wall of the valve mechanism forms a fluid inlet having a diameter substantially equal to the inside diameter of the tube.

15. The apparatus of claim 11, wherein the inverted funnel comprises:
a substantially conical body having an upper opening and a bottom opening, wherein the bottom opening has a diameter greater than the upper opening and wherein the diameter of the bottom opening is substantially equal to the diameter of the fluid inlet.

16. The apparatus of claim 15, wherein the upper opening of the funnel is elevated above the lowest point inside the tube.

17. The apparatus of claim 16 wherein the sealing device includes a spherical body that has a diameter substantially equal to or greater than the difference between the inner diameter of the tube and the diameter of the upper opening of the funnel.

18. The apparatus of claim 17 wherein the spherical body has a specific gravity greater than the specific gravity of water.

19. The apparatus of claim 16 wherein the sealing device is a reed valve.

20. The apparatus of claim 16 wherein the sealing device is a poppet.

21. The apparatus of claim 16 wherein the sealing device is a flapper valve.

22. The apparatus of claim 11 further comprising a handle connected to the top portion, the handle adapted to be affixed to a tether.

23. The apparatus of claim 11 further comprising an optional extension tube adapted to be connected to the lower wall of the valve mechanism, the extension tube having an inside diameter substantially equal to the inside diameter of the elongated tube and the fluid inlet.

24. The apparatus of claim 15 wherein an annulus formed between the inside wall of the tube and the funnel is a sediment trap.

25. A method of sampling fluid layers, comprising:
inserting a sampling apparatus into the fluid, the sampling apparatus including:
an elongated tube having and upper end and a lower end;
a valve mechanism having an upper wall, a lower wall and a flange located between the upper and lower walls, wherein the upper and lower walls and the flange surround an inverted funnel having a sealing device, and wherein the upper wall is connected to the lower end of the tube, whereby the valve mechanism is elevated above the lowest point on the inside of the tube; and
a top portion connected to the upper end, the top portion having an upper closed end and an open lower end, and a surrounding wall including a spout exposing the interior of the top portion;
collecting fluid layers in their representative layer thickness inside the elongated tube;
collecting undesired sediment in a sediment trap formed between the funnel and the inside wall of the tube;
removing the sampling apparatus from the fluid; and
testing the fluid collected in the tube.

* * * * *